US009827066B2

(12) United States Patent
Abt (10) Patent No.: US 9,827,066 B2
(45) Date of Patent: Nov. 28, 2017

(54) METHODS AND SYSTEMS FOR PULSED ILLUMINATION (71) Applicant: NOVARTIS AG, Basel (CH)

(72) Inventor: Niels Alexander Abt, Winterthur (CH)

(73) Assignee: NOVARTIS AG (CH)

( * ) Notice: Subject to any disclaimer, the term of this patent is extended or adjusted under 35 U.S.C. 154(b) by 0 days.

(21) Appl. No.: 15/051,185

(22) Filed: Feb. 23, 2016

(65) Prior Publication Data
US 2017/0231711 A1 Aug. 17, 2017

Related U.S. Application Data (60) Provisional application No. 62/295,559, filed on Feb. 16, 2016.

(51) Int. Cl.
A61B 3/14 (2006.01)
A61B 90/30 (2016.01)
A61B 90/00 (2016.01)
A61B 3/13 (2006.01)
A61F 9/007 (2006.01)

(52) U.S. Cl.
CPC .............. A61B 90/30 (2016.02); A61B 3/13 (2013.01); A61B 3/14 (2013.01); A61B 90/361 (2016.02); A61B 2090/306 (2016.02); A61F 9/007 (2013.01)

(58) Field of Classification Search
CPC ......... A61B 90/30; A61B 90/361; A61B 3/13; A61B 3/14; A61B 2090/306; A61F 9/007

USPC ........................................ 351/206, 205, 200
See application file for complete search history.

(56) References Cited

U.S. PATENT DOCUMENTS

| 9,320,428 B2 * | 4/2016 | Taylor ...................... A61B 3/13 |
| 2002/0060778 A1 | 5/2002 | Su et al. |
| 2006/0147897 A1 | 7/2006 | Grinvald et al. |
| 2011/0230728 A1 | 9/2011 | Artsyukhovich et al. |
| 2012/0203075 A1 | 8/2012 | Horvath et al. |

OTHER PUBLICATIONS

Henrich, et al.; "The Price for Reduced Light Toxicity: Do Endoilluminator Spectral Filters Decrease Color Contract During Brilliant Blue G-Assisted Chromovitrectomy?" Graefes Arch Clin Exp Ophthalmol (2014) 252:367-374, 8 pgs.
Collier et al.; "Comparison of Light Sources for Potential to Induce Photic Retinal Injury"; Alcon, Inc.; 2005 Abstract; 2 pages.
Claes; "Expanding the Scope of MIVS (with cover sheet)"; 2011 Novartis; GUS11260MS, 6 pgs.

(Continued)

Primary Examiner — Tuyen Tra (57) ABSTRACT

Methods and systems for performing an ophthalmic surgical procedure include pulsed illumination of target tissue. The systems may include an illumination instrument arranged to illuminate tissue at a surgical site during the ophthalmic surgical procedure. A light source provides illumination to the illumination instrument for emission from the illumination instrument toward the surgical site. A controller communicates with the light source and activates the light source to provide illumination pulses at a frequency above the flickering perception in humans and with enough light for cameral exposure and human light perception. The light source pulses to minimize phototoxicity.

17 Claims, 5 Drawing Sheets (56) References Cited

OTHER PUBLICATIONS

Novack; "The Constellation Vision System: Assessing the Improvements in Illumination for Vitreoretinal Surgery"; Retinal Physician, Article Date Feb. 1, 2009, 3 pages.
Ji, et al.; "High Speed Low Photodamage Nonlinear Imaging Using Passive Pulse Splitters"; Nature/Methods; (2008), vol. 5; pp. 197-202.
Nighisaki, et al.; "Stroboscopic Illumination Using Light Emitting Diodes Reduced Phototoxicit in Fluoresence Cell Imaging"; (2006), vol. 41; pp. 191-197.
Awh; "Improving Trhe View for Small-Gauge Vitrectomy"; Stellaris PC: Improved Illumination and visualization for retina surgery; Retina Today Insert; Jul./Aug. 2011; p. 2-6.

* cited by examiner

METHODS AND SYSTEMS FOR PULSED ILLUMINATION

CROSS REFERENCE TO RELATED APPLICATIONS

This application claims the benefit of U.S. Provisional Application No. 62/295,559, filed Feb. 16, 2016, the contents being incorporated herein by reference.

TECHNICAL FIELD

The present disclosure is directed to methods and systems for illumination of a surgical area. More particularly, but not by way of limitation, the present disclosure is directed to methods and systems for pulsed illumination of tissue during a vitreoretinal surgical procedure.

BACKGROUND

Phototoxicity in ophthalmic surgeries is a condition resulting from prolonged exposure to light during an ophthalmic surgical procedure and can result in vision loss, introduce other complications, and delay recovery times. Phototoxicity may result from bright light exposure from an endoilluminator located in close proximity to a retina for a prolonged period of time. Nearly all vitreoretinal procedures require at least some illumination of the surgical field. To reduce the risk of phototoxicity, health care providers typically attempt to keep illumination time and intensity as low as possible during vitreoretinal procedures. However, complex or lengthy procedures increase the risk of phototoxicity in a patient. For complex or lengthy procedures, health care providers may be forced to balance the surgical result and the chance of phototoxicity. Particularly, they may compromise a level of surgical treatment by taking steps or shortcuts to minimize the chance of phototoxicity.

Current efforts to curb the occurrence of phototoxicity include the use of color filters to minimize the direct effects of the light on the sensitive retina tissue. However, color filters also have the adverse effect of coloring the light, changing the color of observed tissue and can have a negative impact on visualization of the tissue. Other efforts to curb the occurrence of phototoxicity include the use of systems that regulate the time and exposure of the retina, or monitor the time and intensity of the endoilluminator. These systems then may alert the health care provider when exposure exceeds certain limits. In response, the + care provider may end the surgical procedure or may reduce the light intensity. Ending a surgical procedure prematurely can adversely impact the surgical success, and reducing the illumination intensity can make visualization more challenging.

SUMMARY

The systems and methods described herein may decrease the occurrence of phototoxicity in vitreoretinal surgeries. For example, by using illumination pulses to illuminate the retina and other ophthalmic tissues instead of a continuous light, a user, such as a health care provider, may have sufficient illumination to perform the surgical procedure and may be able to have reduced adverse effects after prolonged exposure.

In some exemplary aspects, the present disclosure is directed to a vitreoretinal surgical system for performing an ophthalmic surgical procedure. The surgical system may include an illumination instrument sized and configured to illuminate tissue at a surgical site during an ophthalmic surgical procedure. The surgical system may also include a light source arranged to provide illumination to the illumination instrument. A controller may communicate with the light source and may be configured to activate the light source in a manner providing illumination pulses at a frequency above the flickering perception in humans and at an illumination level sufficient to allow a user to perform the ophthalmic surgical procedure.

In some aspects, the surgical system may include a microscope disposed and arranged to provide visualization of the illuminated tissue at the surgical site to the user. The surgical system may also include a console including the light source. The surgical system also may include an optical fiber extending from the console to the illumination instrument and connecting the light source and the illumination instrument. The surgical system may also include a surgical instrument for manipulating tissue at the surgical site, the surgical instrument being attached to and powered by the console. The controller may be arranged to activate the light source to provide illumination pulses within a frequency range of 40 Hz to 1000 Hz. The surgical system may include a camera configured to capture images of the tissue at the surgical site, and the controller may be configured to synchronize a camera exposure time with an illumination pulse. In some implementations, the controller may be configured to synchronize the camera exposure time to occur over two or more illumination pulses. The light source may include one or more of a mercury vapor light source, a xenon light source, an LED, a LASER, a halogen light source, and a krypton light source. The controller may be arranged to activate the light source to provide illumination pulses within a frequency range of 50 Hz to 75 Hz. The time between adjacent illumination pulses may be greater than a time period of a pulse width of each illumination pulse. The time between adjacent illumination pulses may be at least twice the time period of the pulse width.

The present disclosure also discloses methods of illuminating a surgical site that include steps that include, for example, introducing a portion of an illumination instrument through a sclera of an eye; illuminating target tissue in the eye with illumination pulses at a frequency above the flickering perception in humans; and performing a surgical procedure on the illuminated target tissue to treat a vitreoretinal condition.

In some implementations, illuminating target tissue in the eye may include illuminating with illumination pulses having a frequency of illumination pulses within a range of about 40 Hz to 100 Hz. In some implementations, illuminating target tissue in the eye may include providing illumination with illumination pulses having a frequency of illumination pulses such that the time between adjacent illumination pulses may be greater than a time period of a pulse width of each illumination pulse. In yet other implementations, illuminating target tissue in the eye comprises providing illumination with illumination pulses having a frequency of illumination pulses such that time between adjacent illumination pulses may be at least twice the time period of a pulse width of a single illumination pulse. A method of illumination may include controlling at least one of a camera and a light source to synchronize image capture functions of the camera with the illumination pulses. In some instances, a method of illumination may include controlling a camera to synchronize image capture functions to occur over the course of at least two illumination pulses for a captured image.

The present disclosure also discloses vitreoretinal surgical systems that may include an illumination instrument sized and configured to illuminate tissue at the surgical site for an ocular procedure and may include a light source arranged to provide illumination to the illumination instrument for emission from the illumination instrument. A controller may be in communication with the light source and may be configured to activate the light source in a manner providing illumination pulses at a frequency above the flickering perception in humans. In some implementations, a time period of each illumination pulse may be smaller than the time between illumination pulses. The surgical system may also include a microscope oriented relative to the surgical site and arranged to provide visualization of the illuminated tissue at the surgical site to the user.

In some implementations, the controller may be arranged to activate the light source to provide illumination at a frequency in a range of 40 Hz to 100 Hz. In some implementations, the system may include a camera configured to capture images of the tissue at the surgical site. The controller may synchronize a camera exposure time with an illumination pulse.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate example implementations of the systems, devices, and methods disclosed herein and together with the description, serve to explain the principles of the present disclosure.

These figures will be better understood by reference to the following detailed description.

DETAILED DESCRIPTION

For the purposes of promoting an understanding of the principles of the present disclosure, reference will now be made to the example implementations illustrated in the drawings and specific language will be used to describe them. It will nevertheless be understood that no limitation of the scope of the disclosure is intended. Any alterations and further modifications to the described devices, instruments, methods, systems, and any further application of the principles of the present disclosure are fully contemplated as would normally occur to one skilled in the art to which the disclosure relates. In addition, this disclosure describes some elements or features in detail with respect to one or more implementations or Figures, when those same elements or features appear in subsequent Figures, without such a high level of detail. It is fully contemplated that the features, components, and/or steps described with respect to one or more implementations or Figures may be combined with the features, components, and/or steps described with respect to other implementations or Figures of the present disclosure. For simplicity, in some instances the same or similar reference numbers are used throughout the drawings to refer to the same or like parts.

The present disclosure relates generally to surgical systems and methods that illuminate a surgical site, such as, for example, an ophthalmic surgical site, with high intensity pulsed illumination. The examples presented herein are in the context of ophthalmic surgical procedures. However, the scope of the disclosure is not so limited. Rather, content of the present disclosure may be applied other areas of the medical arts. Pulses of the pulsed illumination may have high intensity to provide sufficient illumination for the surgical procedure, and in some instances, the same overall light intensity level of illumination as conventional systems using continuous illumination. In some implementations, image capture of the target tissue by a camera may be synchronized with the illumination pulses to provide illuminated images of the target tissue.

Figure 1:
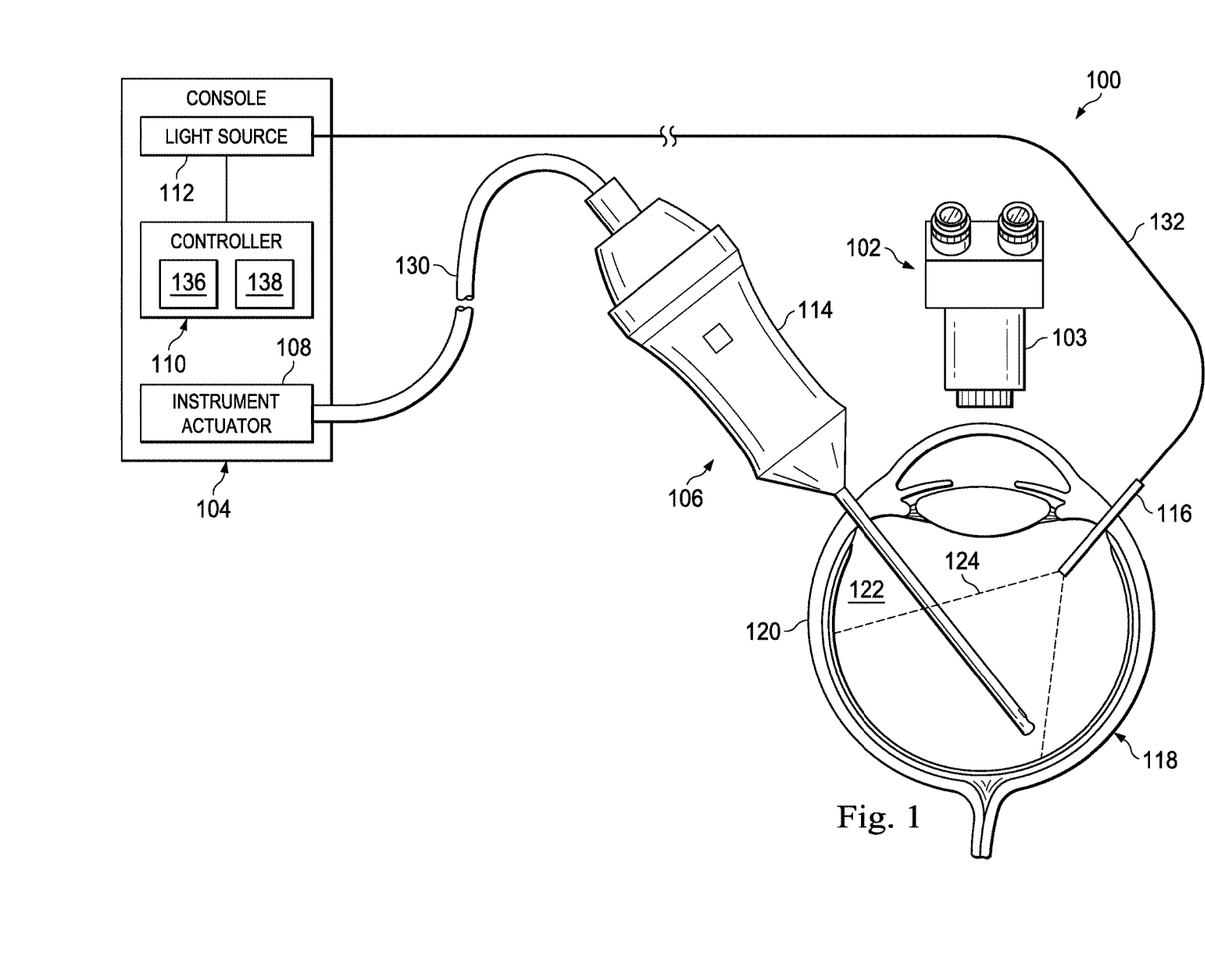
FIG. 1 shows an example vitreoretinal surgical system.

FIG. 1 illustrates a vitreoretinal surgical system, generally designated 100, according to an exemplary implementation. The vitreoretinal surgical system 100 may include features and functionality that allow the vitreoretinal surgical system 100 to be used to perform any of a variety of vitreoretinal procedures. For example, and without limitation, the vitreoretinal surgical system 100 may be used to perform procedures to treat macular degeneration, diabetic retinopathy, diabetic vitreous hemorrhage, a macular hole, a detached retina, epiretinal membrane, CMV retinitis, proliferative vitreoretinopathy generally, trauma, among others. In this exemplary illustration, the vitreoretinal surgical system 100 includes a surgical microscope 102, a console 104, and one or more surgical instruments 106. In some implementations, the vitreoretinal surgical system 100 may include a stand-alone light source with a controller as described herein.

The surgical microscope 102 may be used to visualize and magnify the surgical site. The surgical microscope 102 may include a body portion 103. The body portion 103 may contain lenses, usable for magnification for example, and image processing elements. The image processing elements may be, for example, operable to capture images, converted captures images into a digital format, and display one or more of the captured images on a display. A user may view the displayed images.

The console 104 may be a surgical console used to perform one or more than one surgical processes, such as one or more ophthalmic surgical procedures on a patient. In some implementations, the console 104 may be configured to perform a vitreoretinal procedure, although other procedures are also contemplated. FIG. 1 illustrates a block diagram representing the console 104. In some instances, the console 104 may provide power to, actuate or otherwise activate the one or more surgical instruments 106. The surgical console 104 may include, for example, an instrument actuator 108, a controller 110, and a light source 112. In the exemplary implementation shown, the one or more surgical instruments 106 include a tissue manipulator tool 114 and an illumination instrument 116. In this example, the tissue manipulator tool 114 is a vitrectomy probe. However, the scope of the disclosure is not so limited. Rather, the one or more surgical instruments 106 may include any other surgical instrument or tool for which the console 104 may provide power to, actuate, or activate. For example, the tissue manipulator tool 114 may be one or more of an irrigation device, an aspiration device, or any other instrument. Other manually-operated instruments, such as forceps, spatulas, pics, scissors, and other tissue manipulator tools, that are not powered or otherwise actuated by the console 104 may also be used in the course of a surgical procedure.

The illumination instrument 116 provides light to the surgical site, which in the example in FIG. 1, is shown as an eye 118. In the example shown, the illumination instrument 116 protrudes through the sclera 120 and into the posterior segment 122 of eye 118. In this exemplary implementation, the illumination instrument 116 emits light into the eye 118 so that a user can visualize the tissue in the eye 118 and perform the surgical procedure. Here, the emitted light from the illumination instrument 116 is represented by the reference numeral 124.

The tissue manipulator tool 114 may be in communication with the console 104 via a flexible communication cable 130. In this exemplary implementation, where the tissue manipulator tool 114 is a vitrectomy probe, the communication cable 130 may be formed of, for example, a flexible pneumatic hose. In the case of other types of tissue manipulator tools 114, the communication cable 130 may be selected to perform the desired functionality corresponding to the particular instrument. For example, depending on the implementation and depending on the tissue manipulator tool 114, the cable 130 may be one or more electrical conductors, pneumatic hoses, hydraulic hoses, optical fibers, or other type of communication cable.

The illumination instrument 116 may be configured to introduce light and illuminate tissue in the eye 118 so that the eye 118 can be visualized by a user of the surgical microscope 102. In some implementations, the illumination instrument 116 may be a handheld instrument having a portion sized to penetrate the sclera 120. For example, in some implementations, the illumination instrument 116 may be an endoilluminator. In some instances, the illumination instrument 116 may be an illuminated infusion line, an illuminated cannula, or an illumination chandelier. Other illumination instruments are also contemplated. The illumination instrument 116 may be arranged with instrumentalities that may protect the tissue, and particularly the retina, from overly bright light. Example instrumentalities may include spectrum filters, shields, automated light exposure control, as well as others. In the implementation shown, the illumination instrument 116 is attached to the surgical console 104 by an optical fiber 132. The optical fiber 132 may be a flexible fiber, permitting the illumination instrument 116 to be manipulated or located as desired by a user. Some implementations include insulative or protective sheaths or coatings that protect the optical fiber 132. The optical fiber 132 may be arranged to direct light from the console 104 to the illumination instrument 116 so that the light can be directed into the eye 118 to illuminate the surgical site.

The instrument actuator 108 in the surgical console 104 may be configured and arranged to drive the tissue manipulator tool 114. For example, in the instance where the tissue manipulator tool 114 is a vitrectomy probe, the instrument actuator 108 may be a pneumatic source with one or more valves that provide pressurized air to the vitrectomy probe or a power source to power a drive mechanism of the vitrectomy probe, e.g., a motor or piezoelectric motor. In still other instances, the instrument actuator 108 may be any other type of energy source or actuator that the tissue manipulator tool 114 may utilize. In other implementations, the instrument actuator 108 may provide electrical power to an on-board motor or actuator on the tissue manipulator tool 114. In other implementations, the instrument actuator 108 may be an aspiration pump, irrigation pump, one or more valves, or other type of actuator.

The light source 112 emits light that may be directed to the illumination instrument 116 via the optical fiber 132. In some implementations, the light source 112 may be a mercury vapor light; a xenon light source; a LASER, such as a mini laser or a super continuum laser; an LED; a halogen light; a krypton light; or other light source. The light source 112 may be selected to provide light having a desired frequency or range of frequencies, intensity, flux, or other luminous quality. In some implementations, the emitted light may be selected to have a desired profile including a specific distribution of the radiation wavelength spectrum, range of the radiation wavelength spectrum, or monochromatic color and at a desired intensity or brightness. In some implementations, the range of the radiation wavelength spectrum may exclude at least some portion of the wavelength spectrum encompassing blue light. In some instances, all or substantially all of the blue light wavelengths may be excluded. In some implementations, one or more filters, such as color filters and/or polarizing filters, may be used to further control the light emitted by the light source 112 in order to manage and regulate the light exposure of the tissue at the eye 118. For example, one or more polarizing filters may be uses to polarize the emitted illumination pulses to reduce glare or reflections and, hence, improve the surgical conditions for a surgeon. The one or more filters may be disposed within the console or within the illumination instrument 116. In some implementations, the light source 112 may be a pulsing light. In some implementations, the pulsed light may be generated mechanically, electrically, or a combination of mechanically and electrically. For example, pulses may be generated by directing light towards a spinning device, such as a spinning mirror, disposed in the path of light emitted by the light source 112. Other methods for making pulses are described further below.

The controller 110 may be configured and arranged to control the light emitted from the illumination instrument 116. In some implementations, the controller 110 controls the light emitted from the illumination instrument 116 by controlling the light source 112, although this disclosure is not so limited. Depending on the implementation, the controller 110 may control the light source 112 by causing the light source 112 to emit a light pulse. In some implementations, the controller 110 may control an electric, electro-acoustical, or mechanical element of the light source 112 that may physically intermittently block the light source to create a perception of flickering or pulsing of the light emitted from the illumination instrument 116. In some implementations, pulsing light may be generated using one or more rotating mirrors, mode-locking, saturation filters, and other technologies that may include or be used to generate ultra-short pulses using a LASER.

The controller 110 may include a processor 136 and a memory 138 utilized to control the light source 112 and/or the illumination instrument 116. The processor 136 may include, for example and without limitation, an integrated circuit with power, input, and output pins capable of performing logic functions. In some implementations, the processor 136 may be in communication with the light source 112 and may receive information or inputs from a user for operating the light source 112. The processor 136 may process received inputs and control the light source 112 based on those inputs. In various implementations, the processor 136 may be a targeted device controller. In such implementations, the processor 136 may be in communication with and may perform specific control functions targeted to the light source 112. In some implementations, the processor 136 may control one or more aspects of the light source 112 and illumination instrument 116. In some implementations, the processor 136 may control multiple components of the console 104 or other elements of the vitreoretinal surgical system 100. In still other implementations, the processor 136 may control only the light source 112 or only the illumination instrument 116. In some implementations, the processor 136 may function to cause the light source 112 to flicker or create light pulses with a particular pulse frequency and may control the length of each pulse and its intensity. In some implementations, the processor 136 may be a microprocessor. In some such implementations, the processor 136 may be programmable to control more than one component of the console 104. In some implementations, the processor 136 may be a special purpose controller configured to control different components that perform different functions.

The memory 138 may include various types of memory including volatile memory, such as, for example, Random Access Memory (RAM), FRAM, or NAND flash memory, and non-volatile memory, such as, for example, solid state storage. The memory 138 interfaces with the processor 136, and the processor 136 may write to and read from the memory 138. In some implementations, the memory 138 may store computer readable instructions that include one or more executable programs that, when executed by the processor 136, cause the controller 110 to perform various functions, including controlling the intensity and pulsation of the light source 112 as described herein.

Figure 2:
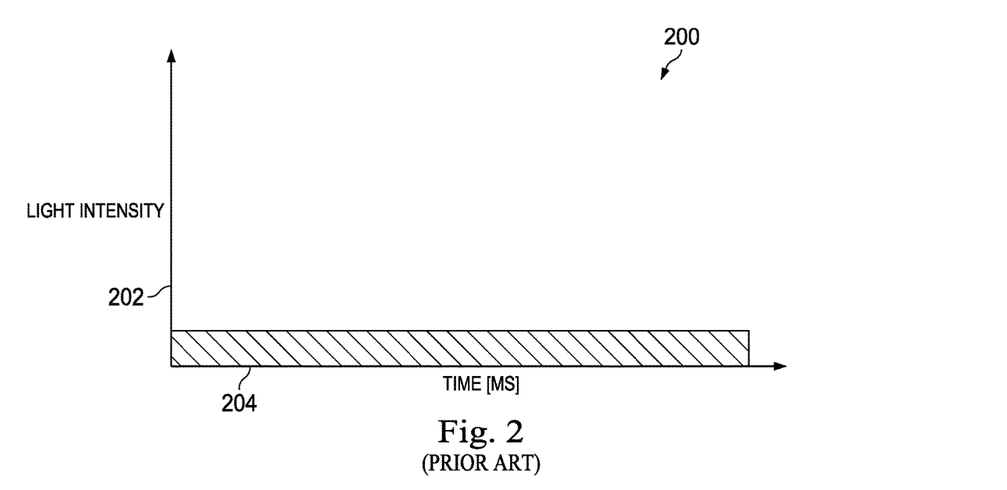
FIG. 2 is a graph showing light intensity relative to time during a conventional vitreoretinal surgery.

FIG. 2 is a graph 200 showing conventional illumination using an illumination instrument during an ophthalmic surgical procedure with light intensity along the y-axis 202 and time along the x-axis 204. During a conventional surgical procedure, illumination instruments are conventionally used to deliver constant and continuous illumination to the surgical site during the course of the surgical procedure. Some conventional illumination instruments provide continuous illumination at a light within a range of about 40 lumens to 70 lumens. This is represented by the flat graph with relatively low intensity shown in FIG. 2.

Figure 3:
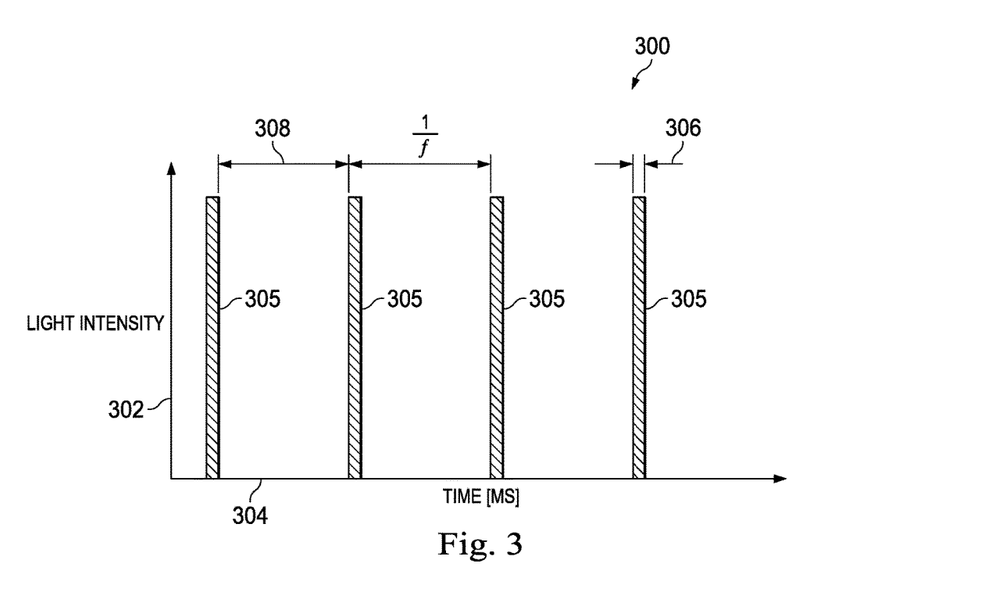
FIG. 3 is a graph showing light intensity relative to time during an ophthalmic surgery procedure using the vitreoretinal surgical system of FIG. 1.

FIG. 3 is a graph 300 showing illumination that may be output from the illumination instrument 116 during an ophthalmic surgical procedure in accordance with the principles described herein. The graph 300 includes intensity along the y-axis 302 and time along the x-axis 304. As can be understood with reference to the graph 300, during an ophthalmic surgical procedure, the illumination instrument 116 may output relatively high intensity light pulses 305 for short periods of time to illuminate the surgical site.

The graph 300 shows a light pulse width (or time that the illumination is on) represented by the numeral 306. The graph 300 also shows a rest width or time between adjacent light pulses 305 (or time that the illumination is off) represented by the numeral 308. Here, the time period of the pulse width 306 is considerably smaller than the time period of the rest width 308, and the light intensity of the light pulse 305 is considerably greater in FIG. 3 than the continuous light intensity in FIG. 2. By using light pulses, instead of continuous illumination as is shown in the graph 200 in FIG. 2, the risk of phototoxicity of the retina may be decreased, even when the light pulses have a higher intensity than the continuous illumination shown in the graph 200 of FIG. 2.

In some implementations, the illumination pulse intensity is selected to provide sufficient illumination to the surgical site for a user of a surgical microscope, such as surgical microscope 102, to perform the surgical procedure. Because the light pulses 305 have a very short pulse width, the intensity may be increased to still provide sufficient light to the surgical site. In some examples, the intensity of the light pulses 305 in the graph 300 is selected so that the number of photons generated and emitted toward the surgical site during pulsed illumination is still equal to the number of photons generated and emitted during the constant and continuous illumination in the graph 200. In other words, in some implementations, the cumulative area under light pulses 305 shown the graph 300 in FIG. 3 over a particular time period is equal to the area defined by the continuous illumination shown in the graph 200 in FIG. 2 over the same time period. While the cumulative light intensity exposure over a given time period for both the pulsed illumination (that is, the cumulative light intensity for all pulses over a given time period) and the continuous illumination is the same, phototoxicity may still be reduced using pulsed illumination.

The following description provides examples showing how pulsed illumination may provide the same overall level of light intensity as provided by conventional continuous illumination. For example, as indicated above, some conventional illumination instruments provide continuous illumination at an overall light intensity level within a range of about 40 lumens to 70 lumens. By balancing the pulse frequency, pulse width, and pulse intensity, similar overall light intensity levels may be obtained using pulsed illumination as compared to continuous illumination. For example, the overall light intensity may be calculated using the equation below.

$$\text{overall light intensity} = \text{frequency} * \text{pulse width} * \text{pulse intensity}$$

For example only, some implementations of pulsed illumination consistent with the principles herein use a light intensity in a range of about 150 lumens with a pulse width of less than 10 ms at a pulse frequency of 40 Hz to achieve an equivalent light output to that of conventional, continuous illumination systems (e.g., in the range of about 40 lumens to 70 lumens). Applying this to the equation above, the overall light intensity=40 Hz*0.010 seconds*150 lumens=60 lumens. As can be seen, the overall light intensity of the pulsed illumination (60 lumens) is within the range of conventional continuous illumination systems (40-70 lumens).

Two additional examples illustrating how the controller 110 may balance pulse settings to achieve a desired overall light intensity level are described below. In a first example, a user may desire an overall light intensity level of 50 lumens, with a pulse frequency of about 50 Hz, and with a pulse width of about 10 ms. The controller 110 may then determine the pulse intensity necessary to obtain the overall light intensity level of 50 lumens. By manipulating the equation above to solve for pulse intensity, the controller 110 may determine that the pulse intensity should be 100 lumens to obtain the desired overall light intensity of 50 lumens. (50 lumens/(50 Hz*0.010 second)=100 lumens).

In a second example, a user may again desire an overall light intensity of 50 lumens, a pulse frequency of about 50

Hz and with a time period of a pulse width of about 1 ms. Again, by manipulating the equation above to solve for pulse intensity, the controller 110 may determine that the pulse intensity should be 1000 lumens to obtain the desired overall light intensity of 50 lumens. (50 lumens/(50 Hz*0.001 second)=1000 lumens).

Accordingly, the controller 110 may balance parameters to obtain a desired overall light intensity. In some implementations, the controller 110 may automatically determine or identify a suitable frequency, pulse width, and pulse intensity to provide the desired overall light intensity. In some implementations, the controller 110 may take into account the type of surgical procedure, physiological factors relating to the specific patient, preferences of the user, and/or other factors to determine suitable settings to achieve a desired overall light intensity during pulsed illumination.

In some implementations, the controller 110 may set the pulse frequency greater than 40 Hz. Because frequencies of 40 Hz and greater are considered to be beyond the range of the flickering perception in humans, the pulses may be substantially imperceptible to a user, such as a surgeon or other health care provider, performing a surgical procedure. In some implementations, the pulse frequency may be in the range of about 40 Hz to 50 Hz. Some implementations may have illumination light pulses in the frequency range of 50 Hz to 1000 Hz. In some implementations, pulse frequencies may be within the range of about 40 Hz to 100 Hz; within the range of about 50 Hz to 100 Hz; within the range of about 50 Hz to 75 Hz; or within the range of about 60 Hz to 75 Hz. Higher and lower frequency ranges may also be utilized.

In some implementations, the controller 110 may establish the time period of the pulse width to be in the range of 0.1 μs to 10 ms. In some implementations, the time period of the pulse width may be less than 10 ms. In some implementations, the time period of the pulse width may be less than 0.1 ms. Time periods of even smaller pulse widths are also within the scope of the disclosure.

The pulse intensity may be selected by balancing the frequency and pulse width, and may also depend on the capabilities of a selected pulse generator or illumination source. Depending on the implementation, pulse intensity may be selected to be within a range of 50 lumens to 70 lumens. In other implementations, pulse intensity may be within the range of 70 lumens or greater. In some implementations, pulse intensity may be selected to be within a range of 80 lumens to 2000 lumens. In still other implementations, pulse intensity may be selected to be within a range of 80 lumens to 500 lumens, within a range of 80 lumens to 200 lumens, or within a range of 100 lumens to 150 lumens. Other ranges are also contemplated.

Referring again to FIG. 3, graph 300 illustrates that the rest width between adjacent light pulses 305 is greater than the pulse width of each light pulse 305. Therefore, in the example illumination pattern illustrated in FIG. 3, the illumination may be off for a longer time period than on. This may be indicated by comparing the pulse width 306 to the rest width 308. In FIG. 3, the time period of the rest width 308 is considerably smaller than the time period of the pulse width 306. The rest width 308 may provide recovery time for the patient's eye, and thereby may reduce the likelihood of phototoxicity. In some implementations, the time period of the rest width 308 may be at least two times greater than the time period of the pulse width 306. The time period of the rest width 308 may be within the range of about two to 40 times greater than the time period of the pulse width 306 in some instances; within the range of 10 to 30 times greater than the time period of the pulse width 306 in some instances; or within the range of 10 to 20 times greater than the time period of the pulse with 306 in still other instances. In other implementations, the time period of the rest width 308 is in the range of about two to 10 times greater than the time period of the pulse width 306. Further, the time period of the rest width 308 may be in the range of about four to eight times greater than the time period of the pulse width 306. A pulse width 306 within the scope of the present disclosure may provide surgical and recovery advantages to the patient. In still other implementations, the relationship between the pulse width 306 and rest width 308 may be sinusoidal in which the pulse width 306 and rest width 308 have approximately the same time periods.

Some implementations utilize light pulses 305 with an intensity in a range of about 80 lumens to 600 lumens at a pulse frequency within a range of about 40 Hz to 100 Hz and a time period of the rest width 308 being more than double the time period of the pulse width 306. In some instances, light pulses 305 may have an intensity within a range of about 100 lumens to 500 lumens at a pulse frequency within a range of about 50 Hz to 100 Hz and a time period of the rest width 308 more than double the time period of the pulse width 306. In still other instances, light pulses 305 may have an intensity within a range of about 500 lumens to 1000 lumens at a pulse frequency within a range of about 50 Hz to 75 Hz and a time period of the rest width 308 more than double the time period of the pulse width 306. Yet other relationships are contemplated and may be selected based on the desired level of illumination intensity desired during a procedure.

While the light pulses 305 shown in the graph 300 show the light intensity returning to zero levels between pulses (e.g., during rest widths 308), some implementations include rest widths during which the light intensity does not fully return to zero. For example only, some implementations may include rest widths 308 in which the light intensity reduces to approximately 10 lumens between light pulses 305. Other intensity levels during the rest widths 308 are also contemplated. In addition, while the light pulses 305 in FIG. 3 are shown to be equally spaced apart in time, the scope of the disclosure is not so limited. Rather, in some implementations, the light pulses 305 may be separated by time periods that are not equally spaced in time. In still other implementations, the light pulses 305 may have time periods between light pulses 305 of different durations. Thus, the rest widths 308 may be varied in both frequency and duration. A variation in frequency and/or duration of the rest widths 308 results in variation of the frequency of the light pulses 305.

In use, the controller 110 may execute a program to operate the light source 112 and/or the illumination instrument 116 to generate light pulses at a desired intensity, with a desired pulse width, and at a desired pulse frequency. These parameters of the generated light pulses may be selected based on, for example, the type of the vitreoretinal surgery being performed, the expected length of the surgery, patient-based physiological criteria, user preferences, and/or other factors. In some implementations, illumination pulse parameters are input by a user based on a surgical plan. In some implementations, the controller 110 selects the parameters for the illumination pulses based on input information discussed above (e.g., the type of the vitreoretinal surgery being performed, the expected length of the surgery, patient-based physiological criteria, preferences of the user, and/or other factors). In some implementations, a user may select only the desired overall light intensity level, and the controller 110 may determine a suitable frequency, pulse width, and pulse intensity to provide the desired overall light intensity level. In some implementations, the controller 110 may include a table with settings corresponding to selectable desired overall light intensity levels. Accordingly, when the user selects an overall light intensity level, the controller 110 may access the table and control the light source according to the settings contained in the table in order to provide the desired pulsed illumination.

The controller 110 may then send signals to activate the light source 112 and/or illumination instrument 116 to generate light pulses according to the desired parameters. In some instances, the controller 110 may determine the parameters of the light pulses based on surgical parameter models previously established and programmed into the controller. For example, in some implementations, rather than selecting a one or more of a particular intensity, frequency, or pulse width of the illumination pulses, a user may select a phototoxicity level not to be exceeded, and a controller may select one or more of the intensity, frequency, or pulse width of the pulsed illumination in order to achieve a total illumination intensity level within the selected constraints, e.g., a phototoxicity level less than or equal to the selected phototoxicity level. In some instances, a user may select an acceptable range of phototoxicity, and the controller would adjust one or more of the intensity, frequency, or pulse width of the illumination pulses in order to generate a total illumination intensity level within the selected phototoxicity range.

Figure 4:
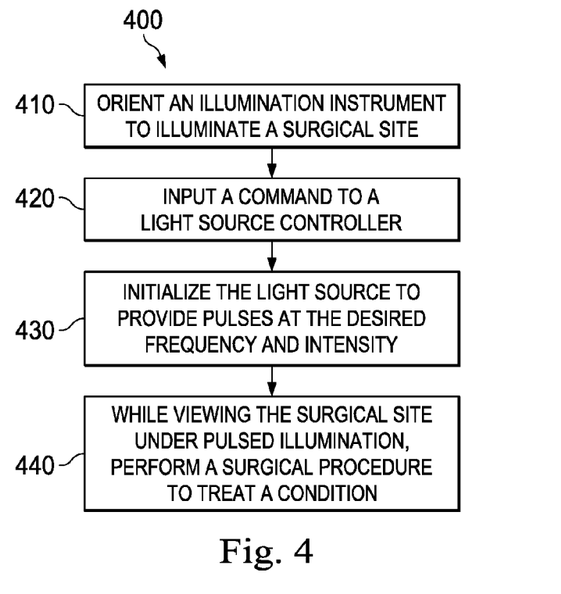
FIG. 4 is a flow chart of an example method of performing an ophthalmic surgical procedure.

FIG. 4 shows an exemplary process 400 for providing illumination of a surgical site. At 410, a user may orient the illumination instrument so that the illumination instrument is arranged to emit light toward a region to be illuminated, such as a retina or tissue around the retina. In some instances, this may include penetrating the globe of an eye with the illumination instrument so that the illumination instrument extends into a posterior segment of an eye. The described methods may also be used to illuminate other regions of the eye. Additionally, the methods described herein are not limited to ophthalmology. Rather, the systems and methods described herein may be used to illuminate other cavities or regions of a patient's body.

At 420, with the illumination instrument in place, the user may input a command to the controller. In some implementations, the input may include a setting for desired illumination intensity, desired time period of a pulse width, and a desired pulse frequency. In some implementations, the user may input a particular type of surgical procedure and the controller may access the memory to identify pulse parameters, such as illumination intensity, a time period of a pulse width, and pulse frequency that may be associated with the selected type of procedure. In some implementations, the controller may operate using an algorithm that optimally adjusts the illumination intensity, the time period of the pulse width, the pulse frequency or other parameters with a single input. For example only and without limiting the scope of this disclosure, a user may input an adjustment regarding the perceived brightness, and the controller then automatically makes additional parameter adjustments to one or more settings to achieve the desired brightness level.

At 430, in response to the input, the controller initializes the light source to provide illumination pulses at the desired pulse frequency, pulse width, and intensity. In some instances, the light pulse may be arranged to be a high intensity light of 200 lumens at a pulse frequency greater than about 40 Hz, and with a time period of a rest width at least twice the time period of the pulse width. Depending upon the implementation, the time period of the pulse width may be selected to be less than 10 ms, less than 1 ms, less than 10 µs, less than 1 µs, or any other desired pulse width. In some implementations, the light pulse is a high intensity light emitting greater than 100 lumens. In some implementations, the light pulse may have an intensity in a range of 100 lumens to 500 lumens. In some implementations, the light pulse may have an intensity in a range of 70 lumens to 150 lumens. The frequency of the light pulses may be adjusted based on the time period of the pulse width and pulse intensity to provide the overall desired intensity. In some instances, the overall desired intensity may fall within the range of about 40 lumens to 70 lumens, which may be considered an acceptable overall surgical illumination range. Yet other ranges of intensity, time period of a pulse width, and pulse frequency are contemplated. At 440, the user views the surgical site through the microscope and performs a surgical procedure to treat a condition.

Figure 5:
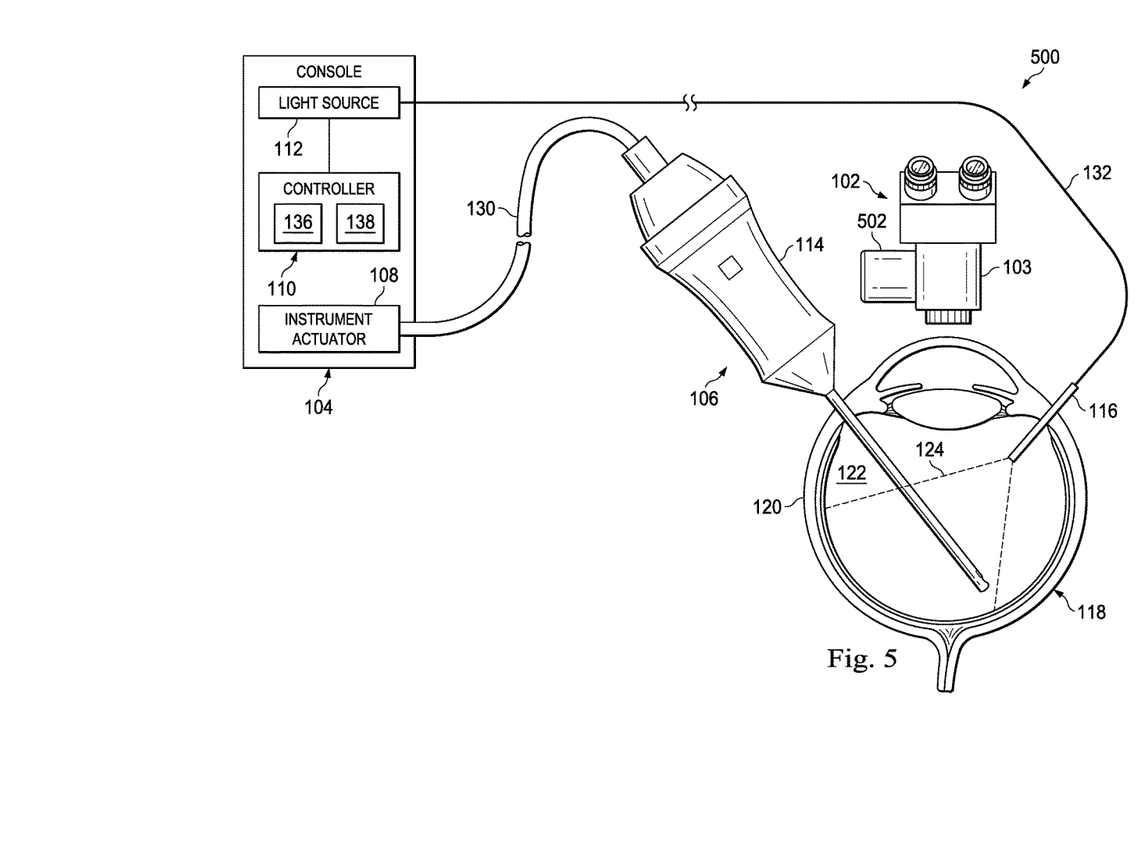
FIG. 5 is an illustration of the vitreoretinal surgical system of FIG. 1 including a camera.

FIG. 5 shows a vitreoretinal surgical system 500 that includes a camera 502 disposed on, coupled to, or cooperating with the surgical microscope 102. The vitreoretinal surgical system 500 includes many features similar to the vitreoretinal surgical system 100 described above. While the following discussion will address additional features of the vitreoretinal surgical system 500 not included in the vitreoretinal surgical system 100, it should be noted that the description above with respect to vitreoretinal surgical system 100 also applies to the vitreoretinal surgical system 500 in FIG. 5.

The camera 502 may be configured to take and capture photographs or video of the surgical site, which in this example is the eye 118. The camera 502 may be associated with the surgical microscope 102 in a manner permitting the camera 502 to capture images of the surgical site as viewed through the surgical microscope 102. In some implementations, the camera 502 may communicate captured images to the console 104 for storage in the memory 138. In some implementations, the images may be stored elsewhere, including onboard the camera 502. In some implementations, the images may be communicated and displayed directly on a display screen that may be viewable by the user or others.

The camera 502 may be in communication with the controller 110, and the controller 110 may be configured to synchronize a camera exposure time with the illumination pulses so that the camera 502 can obtain well-lit images for satisfactory visualization. For example, the controller 110 may operate to synchronize the camera exposure time with the illumination pulses so that the captured images are not taken between illumination pulses with insufficient lighting, but instead, are taken at the times that the tissue is illuminated by a light pulse.

Figure 6:
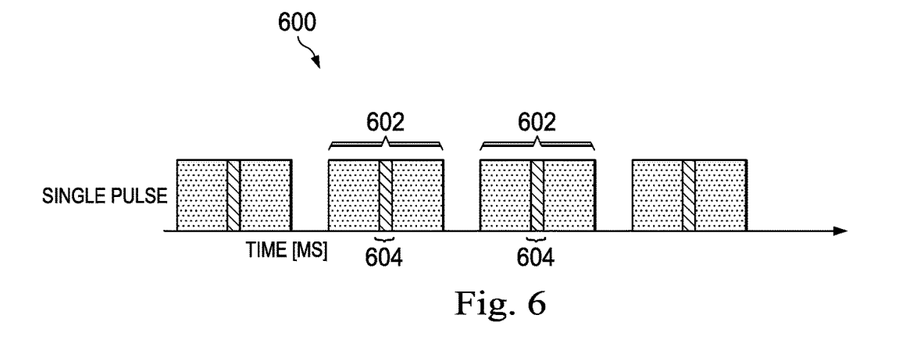
FIG. 6 is a graph showing synchronization of camera exposure time to single illumination pulses that may be used during an ophthalmic surgical procedure.

FIG. 6 is an example graph 600 showing illumination pulses 604 relative to camera exposure times 602 for the camera 502 (FIG. 5). Each illumination pulse 604 may be synchronized by the controller 110 to occur during the camera exposure time 602. Here, the camera exposure time 602 may be longer than the time period of the illumination pulse 604, and may begin before the illumination pulse 604 and may end after the illumination pulse 604. Also, although FIG. 6 shows that the illumination pulse 604 occurs substantially in the middle of the exposure time 602, the scope of the disclosure is not so limited. Rather, the illumination pulse 604 may occur at any time during the exposure time 604. For example, in some instances, the illumination pulse 604 may occur near the start of the exposure time 602. In other instances, the illumination pulse 604 may occur towards the end of the exposure time 602. Thus, the illumination pulse 604 may occur at any time during the exposure time 602.

Figure 7:
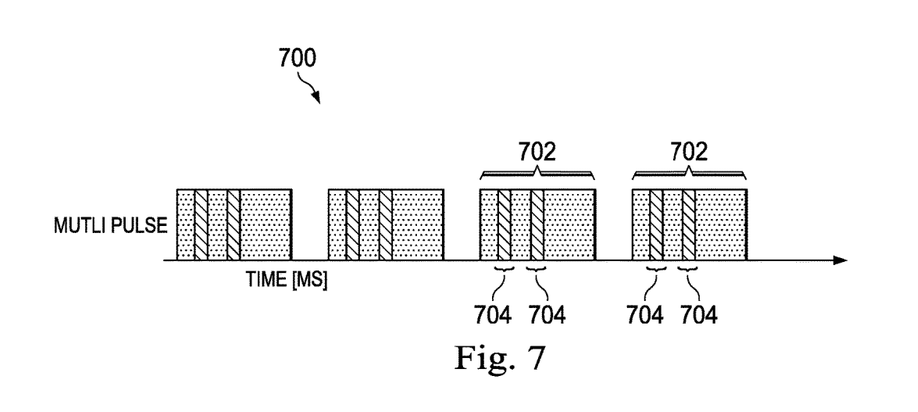
FIG. 7 is a graph showing synchronization of camera exposure time to multiple illumination pulses that may be used during an ophthalmic surgical procedure.

FIG. 7 is a graph 700 showing multiple illumination pulses 704 for a single camera exposure time 702. Here, the controller synchronizes the camera exposure time 702 and the time period of the illumination pulses 704 so that multiple illumination pulses 704 are generated during each camera exposure time 702. While two illumination pulses 704 are shown for each camera exposure time in FIG. 7, other implementations include three illumination pulses or more than three pulses for each camera exposure time 702. Further, the illumination pulses 704 may occur at any time during the exposure time 702.

Figure 8:
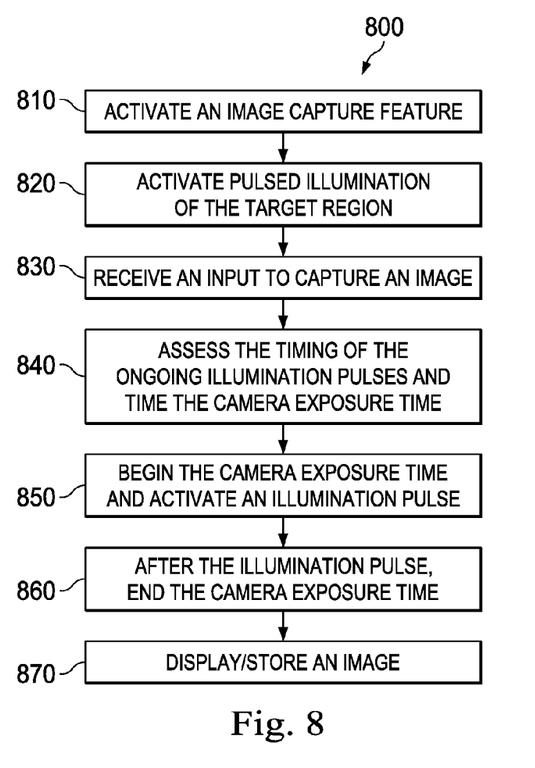
FIG. 8 is a flow chart of an example method of capturing an image during a surgical procedure.

FIG. 8 shows an example method 800 of capturing an image with a vitreoretinal surgical system, such as vitreoretinal surgical system 500 shown in FIG. 5, by controlling a camera, e.g., camera 502 and a light source, e.g., light source 112. In use at 810, a user may activate an image capture feature of the vitreoretinal surgical system to use the camera. Activating an image capture feature may include powering the camera, may include turning on an image capture mode of the vitreoretinal surgical system, or may include taking other action that indicates that the controller should synchronize the camera exposure time and light source actions.

At 820, the controller may activate pulsed illumination of the target tissue. In some implementations, activation of the pulsed illumination may occur, for example, before the illumination instrument is introduced to the surgical site, after being introduced and during placement, or at any other time before, during, or after a surgical treatment. The controller may activate pulsed illumination by controlling the light source to provide the pulsed illumination to the illumination instrument.

With the illumination instrument providing illumination of the surgical site, and at 830, the controller may receive an input to capture an image. The input may be received from a user providing an input to the controller or may be from the camera, which may be controlled or set to capture images either manually or automatically.

At 840, the controller may respond to the input by assessing the timing of the on-going light pulses and synchronizing the camera exposure time. For example, in some implementations, the camera exposure time may be started before an illumination pulse and ended after the illumination pulse. At 850, the controller begins the exposure time on the camera and, during the exposure time, activates at least one illumination pulse. At 860, after the illumination pulse has ended, the controller ends the exposure time. In some implementations, a single light pulse occurs during the camera exposure time. In some implementations, two or more light pulses occur during the camera exposure time. At 870, the image may be displayed to the user and/or stored in the memory. In some implementations, the method may be repeated over and over. In some instances, the example method may occur at the same pulse frequency as the illumination pulses.

By controlling the light source to provide illumination to an ocular surgical site using high intensity pulses at a frequency range to deliver a desired amount of light intensity, the incidence of phototoxicity may be decreased in patients. This may be particularly beneficial in lengthy or complex surgical procedures where users must balance the risk of phototoxicity against the desire to provide careful and complete surgical treatment of the patient. Accordingly, pulsed illumination may increase patient satisfaction and provide better patient outcome.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A vitreoretinal surgical system for performing an ocular treatment procedure, comprising:
   an illumination instrument sized and structurally configured to illuminate tissue at a surgical site during an ocular treatment procedure;
   a light source arranged to provide illumination to the illumination instrument for emission from the illumination instrument toward the surgical site; and
   a controller in communication with the light source and configured to activate the light source in a manner providing illumination pulses at a frequency above a flickering perception in humans and at an illumination level to allow a user to perform the ocular treatment procedure,
   wherein the controller is arranged to activate the light source to provide illumination pulses within a frequency range of 50 Hz to 75 Hz.

2. The vitreoretinal surgical system of claim 1, further comprising a microscope disposed and arranged to provide visualization of illuminated tissue at the surgical site to the user.

3. The vitreoretinal surgical system of claim 1, further comprising:
   a console including the light source; and
   an optical fiber extending from the console to the illumination instrument and connecting the light source and the illumination instrument.

4. The vitreoretinal surgical system of claim 3, further comprising a surgical instrument arranged to manipulate tissue at the surgical site, the surgical instrument being attached to and powered by the console.

5. The vitreoretinal surgical system of claim 1, further comprising a camera configured to capture images of the tissue at the surgical site, the controller being configured to synchronize a camera exposure time with an illumination pulse.

6. The vitreoretinal surgical system of claim 5, wherein the controller is configured to synchronize the camera exposure time to occur over two or more illumination pulses.

7. The vitreoretinal surgical system of claim 1, wherein the light source comprises at least one of a mercury vapor light source, a xenon light source, an LED, a LASER, a halogen light source, and a krypton light source.

8. The vitreoretinal surgical system of claim 1, wherein time between adjacent illumination pulses is greater than a time period of a pulse width of each illumination pulse.

9. The vitreoretinal surgical system of claim 8, wherein the time between adjacent illumination pulses is at least twice the time period of the pulse width.

10. A method of illuminating a surgical site, comprising:
    introducing a portion of an illumination instrument into an eye;

illuminating, with the illumination instrument, target tissue in the eye with illumination pulses at a frequency above the flickering perception in humans; and performing a surgical procedure on the eye.

11. The method of claim 10, wherein illuminating the target tissue in the eye comprises illuminating with illumination pulses having a frequency of illumination pulses within a frequency range of about 40 Hz to 100 Hz.

12. The method of claim 10, wherein illuminating target tissue in the eye comprises providing illumination with illumination pulses having a frequency of illumination pulses such that time between adjacent illumination pulses is greater than a time period of a pulse width of each illumination pulse.

13. The method of claim 10, wherein illuminating target tissue in the eye comprises providing illumination with illumination pulses having a frequency of illumination pulses such that time between adjacent illumination pulses is at least twice the time period of an illumination pulse width of a single illumination pulse.

14. The method of claim 10, further comprising controlling one of a camera and a light source to synchronize image capture functions of the camera with the illumination pulses.

15. The method of claim 10, further comprising synchronizing an exposure time of a camera to capture an image such that a duration of the exposure time occurs over the course of at least two illumination pulses.

16. A vitreoretinal surgical system for performing a vitreoretinal procedure, comprising:
   an illumination instrument sized and configured to illuminate tissue at a surgical site for an ocular procedure;
   a light source arranged to provide illumination to the illumination instrument for emission from the illumination instrument;
   a controller in communication with the light source and configured to activate the light source in a manner providing illumination pulses at a frequency above a flickering perception in humans, and wherein a time period of each illumination pulse is smaller than the time between illumination pulses; and
   a microscope oriented relative to the surgical site and arranged to provide visualization of illuminated tissue at the surgical site to a user,
   wherein the controller is arranged to activate the light source to provide illumination at a frequency in a range of 40 Hz to 100 Hz.

17. The vitreoretinal surgical system of claim 16, comprising a camera configured to capture images of the tissue at the surgical site, the controller being configured to synchronize a camera exposure with an illumination pulse.

* * * * *